April 18, 1950 L. A. BRADY Plant Pat. 932

ROSE PLANT

Filed Jan. 17, 1949

Inventor
L. A. Brady
By Robb & Robb
Attorneys

Patented Apr. 18, 1950

Plant Pat. 932

UNITED STATES PATENT OFFICE

932

ROSE PLANT

Lee A. Brady, Tyler, Tex., assignor to The Conard-Pyle Company, West Grove, Pa., a corporation of Pennsylvania Application January 17, 1949, Serial No. 71,281

1 Claim. (Cl. 47—61)

The present discovery relates to a new and distinct variety of rose plant, originating as a sport of the rose "Peace" (Plant Patent No. 591) and distinguishable therefrom dominantly by its climbing habit.

The parent plant is a bush rose of the hybrid tea class and is notable for its exceptionally strong growing habit, the distinguished appearance of its large foliage and the distinctive combination of size, form and unusual blend of coloring in the blooms.

Of primary importance here, however, is the fact that this parent variety maintains a definite bush form with strong, rigid, upright canes, its growth being that of a strong and vigorous bush rose.

As distinguished from this, the canes on this new sport are of a distinctly different type of growth. That is to say, they grow much longer and much more rapidly than the parent. For example, on a year-old plant they average more than twice the length of the canes of the bush rose plants of the same age. These long, climbing canes show little branching the first year, are heavy but limber, starting from the ground at a slight slant, arching gracefully and requiring support if they are to be kept upright.

Figure 2:
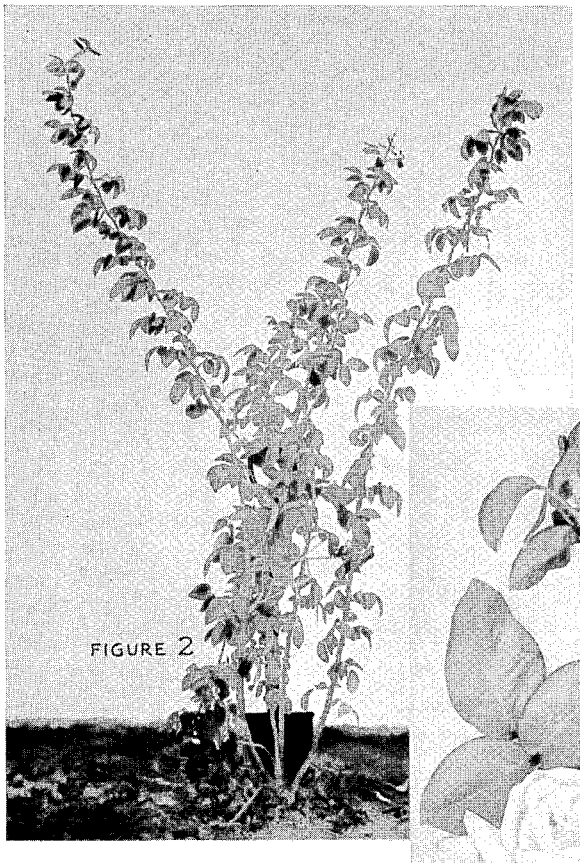
Figure 1:
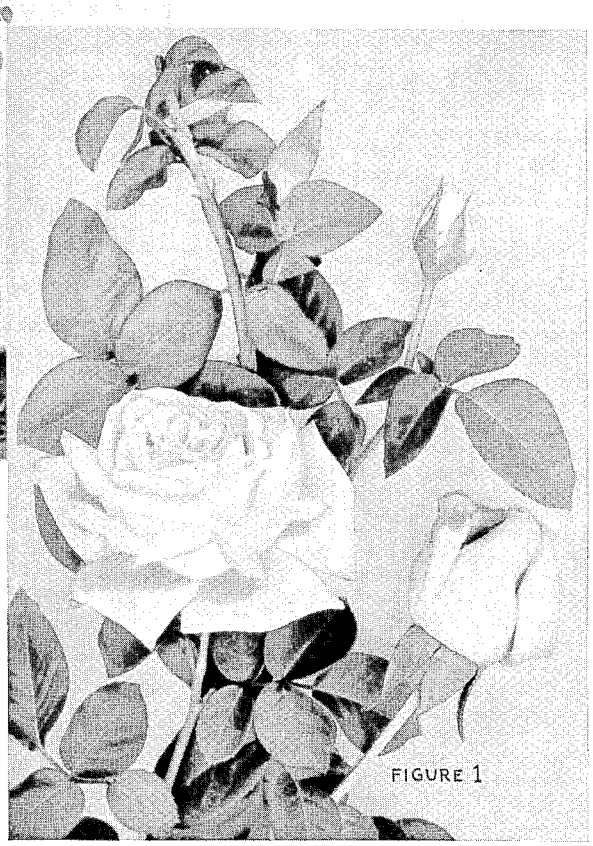

In the accompanying drawing, Figure 1 shows specimens of the blooms from a one-year-old plant of this new variety; and Figure 2 illustrates the first year growth of a specimen plant, its size shown in comparison with the nursery shovel placed directly behind the plant. These illustrations were taken to show the length of growth made by these plants their first year.

Aside from this climbing habit, the new variety has the same general characteristics that are present in its parent bush variety, having reference to its foliage, color of buds and flowers, etc. It is, therefore, unnecessary to describe the plant in detail, since it conforms to the description contained in the previously named patent for the parent variety, excepting only the parent's habit of growth as a bush.

The new variety has been carefully tested ever since its discovery. It has been repeatedly reproduced asexually by budding, and the climbing characteristics noted appeared to be fully established and transmitted to the progeny.

I claim:

A new and distinct variety of rose plant, having the same characteristics as its parent (Plant Patent 591) in respect to its foliage, the large size, form and distinctive coloring of its bud and flower, but distinguished therefrom by its strong and vigorous climbing habit, substantially as shown and described.

LEE A. BRADY.

No references cited.